US008900297B2

(12) United States Patent
Schlueter

(10) Patent No.: US 8,900,297 B2
(45) Date of Patent: *Dec. 2, 2014

(54) OPHTHALMIC AND OTORHINOLARYNGOLOGICAL DEVICE MATERIALS

(71) Applicant: Novartis AG, Basel (CH)

(72) Inventor: Douglas C. Schlueter, Azle, TX (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/228,679

(22) Filed: Mar. 28, 2014

(65) Prior Publication Data
US 2014/0213733 A1    Jul. 31, 2014

Related U.S. Application Data

(63) Continuation of application No. 13/211,416, filed on Aug. 17, 2011, now Pat. No. 8,728,157, which is a continuation of application No. 12/244,814, filed on Oct. 3, 2008, now Pat. No. 8,048,154.

(60) Provisional application No. 60/978,000, filed on Oct. 5, 2007.

(51) Int. Cl.
| A61F 2/16 | (2006.01) |
| A61F 2/14 | (2006.01) |
| C08F 118/02 | (2006.01) |
| C08F 22/10 | (2006.01) |
| C08F 122/10 | (2006.01) |
| C08F 222/10 | (2006.01) |
| C08F 20/10 | (2006.01) |
| G02B 1/04 | (2006.01) |
| A61L 27/16 | (2006.01) |
| A61L 27/50 | (2006.01) |

(52) U.S. Cl.
CPC ................ *G02B 1/041* (2013.01); *A61L 27/16* (2013.01); *A61L 27/50* (2013.01); *A61F 2/16* (2013.01)
USPC .......... 623/6.11; 623/4.1; 623/5.12; 526/319; 526/321; 526/323.1

(58) Field of Classification Search
USPC ............... 526/319, 321, 323.1; 623/6.11, 4.1, 623/5.12
See application file for complete search history.

(56) References Cited

U.S. PATENT DOCUMENTS

| 3,842,059 A | 10/1974 | Milkovich et al. |
| 3,862,077 A | 1/1975 | Schulz et al. |
| 5,290,892 A | 3/1994 | Namdaran et al. |
| 5,331,073 A | 7/1994 | Weinschenk, III et al. |
| 5,391,628 A | 2/1995 | Gaillard et al. |
| 5,693,095 A | 12/1997 | Freeman et al. |
| 5,763,548 A | 6/1998 | Matyjaszewski et al. |
| 5,789,487 A | 8/1998 | Matyjaszewski et al. |
| 5,852,129 A | 12/1998 | Kusakabe et al. |
| 6,221,991 B1 | 4/2001 | Letchford et al. |
| 6,353,069 B1 | 3/2002 | Freeman et al. |
| 6,528,602 B1 | 3/2003 | Freeman et al. |
| 6,653,422 B2 | 11/2003 | Freeman et al. |
| 6,806,337 B2 | 10/2004 | Schlueter et al. |
| 7,390,863 B2 | 6/2008 | Salamone et al. |
| 7,652,076 B2 | 1/2010 | Schlueter et al. |
| 7,888,403 B2 | 2/2011 | Schlueter et al. |
| 2006/0134169 A1 | 6/2006 | Linhardt et al. |
| 2006/0275342 A1 | 12/2006 | Lindhardt et al. |
| 2006/0282163 A1 * | 12/2006 | Schlueter et al. ............ 623/6.11 |

FOREIGN PATENT DOCUMENTS

| JP | 10-504059 | 4/1998 |
| JP | 2002-511597 | 4/2002 |
| JP | 2003-508187 | 3/2003 |
| JP | 2005-533153 | 11/2005 |
| WO | 96/40303 | 12/1996 |
| WO | WO9724382 | 10/1997 |
| WO | 99/53347 | 10/1999 |
| WO | 01/18078 | 3/2001 |
| WO | 2004/007579 | 1/2004 |
| WO | 2006/019404 | 2/2006 |
| WO | WO2006063139 A3 | 6/2006 |
| WO | WO2006130402 A2 | 7/2006 |
| WO | WO2006138188 A1 | 12/2006 |
| WO | WO2006138213 A1 | 12/2006 |

OTHER PUBLICATIONS

Neugebauer, et al., Densely-Grafted and Double-Grafted PEO Brushes via ATRP. A Route to Soft Eleastomers, Macromolecules, 2003, 6745-6755, 36, ACS Publications, Washington, DC.
Ishizu, et al., Aggregation behaviors of AB-type brush-block-brush amphiphilic copolymers in aqueous media, Journal of Materials Science, 2004, 4295-4300, 39, Kluwer Academic Publishers.
Kurjata, et al., Synthesis of poly[dimethylsiloxane-block-oligo (ethylene glycol) methyl ether methacrylate]: an amphiphilic copolymer with a comb-like block. Polymer, 2004, 6111-6121, 45.
Wang, et al., Facile Atom Transfer Radical Polymerization of Methoxy-Capped Oligo (ethylene glycol) Methacrylate in Aqueous Media at Ambient Temperature. Macromolecules, 2000. 6640-6647, 33, ACS Publications, Washington, DC.
Norman, et al. Synthesis of Well-Defined Macromonomers by Sequential ATRP-Catalytic Chain Transfer and Copolymerization with Ethyl Acrylate, Macromolecules 2002, 8954-8961, 35 (24), ACS Publications, Washington, DC.
Bon, et al., Modification of the w-Bromo End Group of Poly (methacrylate)s Prepared by Copper (I)-Mediated Living Radical Polymerization. Journal of Polymer Science: Part A: Polymer Chemistry, 2000, 2678-2686, 38, John Wiley & Sons, Inc.
Chen, et al. Synthesis of acrylic macromonomers by free-radical-initiated polymerization. Conversion to comblike polymers. Macromolecules, 1991, 2151-2155, 24, ACS Publications, Washington, DC.

* cited by examiner

*Primary Examiner* — Karuna P Reddy
(74) *Attorney, Agent, or Firm* — Patrick M. Ryan

(57) ABSTRACT

Disclosed are soft, high refractive index, acrylic device materials. The materials contain a hydrophilic side-chain macromer for glistening resistance.

13 Claims, No Drawings

OPHTHALMIC AND OTORHINOLARYNGOLOGICAL DEVICE MATERIALS

This application is a continuation application of U.S. Ser. No. 13/211,416, filed Aug. 17, 2011, which is a continuation application of U.S. Ser. No. 12/244,814, filed Oct. 3, 2008, which claims priority to U.S. Provisional application, U.S. Ser. No. 60/978,000, filed Oct. 5, 2007.

FIELD OF THE INVENTION

This invention is directed to improved ophthalmic and otorhinolaryngological device materials. In particular, this invention relates to soft, high refractive index acrylic device materials that have improved glistening resistance.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Conventional silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than conventional silicone materials.

U.S. Pat. No. 5,290,892 discloses high refractive index, acrylic materials suitable for use as an intraocular lens ("IOL") material. These acrylic materials contain, as principal components, two aryl acrylic monomers. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable, high refractive index ophthalmic lens materials containing at least about 90 wt. % of only two principal components: one aryl acrylic hydrophobic monomer and one hydrophilic monomer. The aryl acrylic hydrophobic monomer has the formula

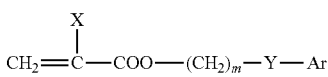

wherein:
X is H or $CH_3$;
m is 0-6;
Y is nothing, O, S, or NR, wherein R is H, $CH_3$, $C_nH_{2n+1}$ (n=1-10), iso-$OC_3H_7$, $C_6H_5$, or $CH_2C_6H_5$; and
Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

The lens materials described in the '095 patent preferably have a glass-transition temperature ("$T_g$") between about −20 and +25° C.

Flexible intraocular lenses may be folded and inserted through a small incision. In general, a softer material may be deformed to a greater extent so that it can be inserted through an increasingly smaller incision. Soft acrylic or methacrylic materials typically do not have an appropriate combination of strength, flexibility and non-tacky surface properties to permit IOLs to be inserted through an incision as small as that required for silicone IOLs.

Polyethylene glycol (PEG) dimethacrylates are known to improve glistening resistance of hydrophobic acrylic formulations. See, for example, U.S. Pat. Nos. 5,693,095; 6,528, 602; 6,653,422; and 6,353,069. Both the concentration and molecular weight of PEG dimethacrylates have an impact on glistening performance. Generally, use of higher molecular weight PEG dimethacrylates (1000 MW) yield copolymers with improved glistening performance at low PEG concentrations (10-15 wt %), as compared to lower molecular weight PEG dimethacrylates (<1000 MW). However, low PEG dimethacrylate concentrations are desirable to maintain a high refractive index copolymer. Addition of PEG dimethacrylates also tends to decrease the modulus and tensile strength of the resulting copolymer. Also, higher molecular weight PEG dimethacrylates are generally not miscible with hydrophobic acrylic monomers.

SUMMARY OF THE INVENTION

Improved soft, foldable acrylic device materials which are particularly suited for use as IOLs, but which are also useful as other ophthalmic or otorhinolaryngological devices, such as contact lenses, keratoprostheses, corneal rings or inlays, otological ventilation tubes and nasal implants, have been discovered. These polymeric materials comprise macromers containing hydrophilic side-chains.

The subject hydrophilic side-chain macromers allow synthesis of glistening resistant, low equilibrium water content, high refractive index IOLs. The use of a macromer having a hydrophilic side-chain allows incorporation of higher molecular weight hydrophilic ingredients into a hydrophobic copolymer formulation. Higher molecular weight hydrophilic ingredients are more efficient glistening resistance ingredients than comparable weight fractions of lower molecular weight hydrophilic polymers. This resulting hydrophilic ingredient concentration reduction results in reduced equilibrium water content, higher refractive index, and a smaller mass intraocular lens that can be inserted through a smaller incision.

DETAILED DESCRIPTION OF THE INVENTION

Unless indicated otherwise, all component amounts are presented on a % (w/w) basis ("wt. %").

The device materials of the present invention are copolymers comprising a) a monofunctional acrylate or methacrylate monomer [1], b) a difunctional acrylate or methacrylate cross-linker [2], and c) a hydrophilic side-chain macromer [3] (which may be a macromer of formula [3a], [3b], [3c], [3d], or [3e]). The device materials may contain more than one monomer [1], more than one monomer [2], and more than one macromer [3]. Unless indicated otherwise, references to each ingredient are intended to encompass multiple monomers or macromers of the same formula and references to amounts are intended to refer to the total amount of all monomers of each formula.

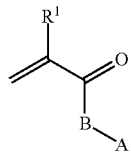
[1]

wherein
- $B = -O(CH_2)_n-, -(OCH_2CH_2)_n-, -NH(CH_2)_n-,$ or $-NCH_3(CH_2)_n-;$
- $R^1 = H, CH_3, CH_2CH_3,$ or $CH_2OH;$
- $n = 0-12;$
- $A = C_6H_5$ or $O(CH_2)_m C_6H_5$, where the $C_6H_5$ group is optionally substituted with $-(CH_2)_n H, -O(CH_2)_n H, -CH(CH_3)_2, -C_6H_5, -OC_6H_5, -CH_2C_6H_5,$ F, Cl, Br, or I; and
- $m = 0-18;$

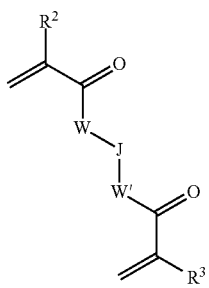
[2]

wherein
- $R^2, R^3$ independently $= H, CH_3, CH_2CH_3,$ or $CH_2OH;$
- $W, W'$ independently $= O(CH_2)_d, NH(CH_2)_d, NCH_3(CH_2)_d, O(CH_2)_d C_6H_4, O(CH_2CH_2O)_d CH_2, O(CH_2CH_2CH_2O)_d CH_2, O(CH_2CH_2CH_2CH_2O)_d CH_2,$ or nothing;
- $J = (CH_2)_a, O(CH_2CH_2O)_b,$ O, or nothing, provided that if W and W' = nothing, then $J \ne$ nothing;
- $d = 0-12;$
- $a = 1-12;$
- $b = 1-24;$

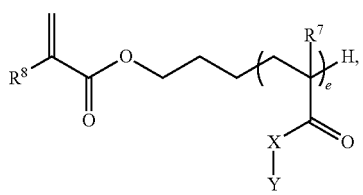
[3a]

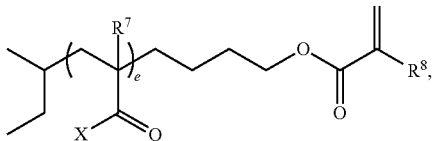
[3b]

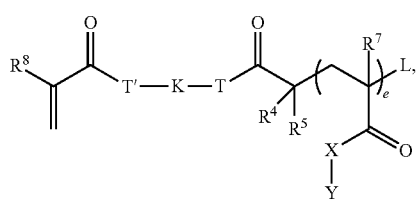
[3c]

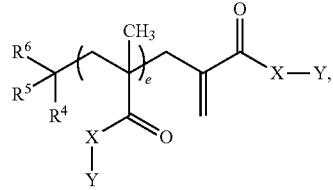
[3d]

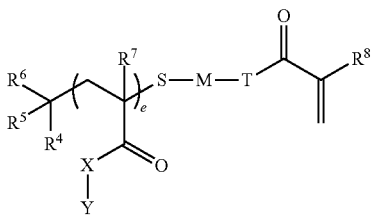
[3e]

wherein for formulas [3a], [3b], [3c], [3d], and [3e] (collectively, "formula [3]")
- $e = 1-50;$
- $X = -O-, -NH-, -N(CH_3)-, -N(CH_2CH_3)-,$ or $-N(C_6H_5)-;$
- $Y = H, -(CH_2)_p OH, -CH_2CH_2N(CH_3)_2, -CH_2CH_2N(CH_2CH_3)_2, -CH_2CH(OH)CH_2OH, -(CH_2CH_2O)_q CH_3, -(CH_2CH_2O)_q H, -(CH_2CH_2O)_q C_6H_5,$ or

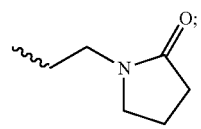

- $p = 1-12;$
- $q = 1-230;$
- $T, T'$ independently $= O(CH_2)_{d'}, NH(CH_2)_{d'}, NCH_3(CH_2)_{d'}, O(CH_2)_{d'} C_6H_4, O(CH_2CH_2O)_d CH_2, O(CH_2CH_2CH_2O)_d CH_2, O(CH_2CH_2CH_2CH_2O)_d CH_2,$ or nothing;
- $K = (CH_2)_{a'}, O(CH_2CH_2O)_{b'},$ O, or nothing, provided that if T and T' = nothing, then $K \ne$ nothing;
- $d' = 0-12;$
- $a' = 1-12;$
- $b' = 1-24;$
- $L = H, Cl, Br, -CH_2C(O)CH_3, CH_2C(O)C(CH_3)_3, -CH_2C(O)C_6H_5, -CH_2C(O)C_6H_4OH, -CH_2C(O)C_6H_4OCH_3,$

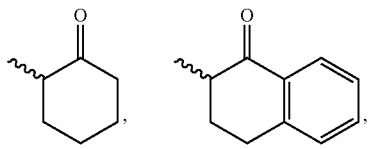

or —CH$_2$CH=CH$_2$;

R$^4$, R$^5$ independently=H, CH$_3$, CH$_2$CH$_3$, CH$_2$CH$_2$CH$_3$, CH(CH$_3$)$_2$, CH$_2$CH$_2$CH$_2$CH$_3$, or CH$_2$CH(CH$_3$)$_2$;

R$_6$=—CO$_2$CH$_3$, —CO$_2$CH$_2$CH$_3$, —CN, or —CONHCH$_2$CH$_2$CH$_2$CH$_3$;

R$^7$, R$^8$ independently=H, CH$_3$, CH$_2$CH$_3$, or CH$_2$OH;

M=—(CH$_2$)$_{a''}$—; and a''=2-20.

Preferred monomers of formula [1] are those wherein:

B=—O(CH$_2$)$_n$— or —(OCH$_2$CH$_2$)$_n$—;

R$^1$=—H or —CH$_3$;

n=1-5;

A=—C$_6$H$_5$, O(CH$_2$)$_m$, C$_6$H$_5$; and m=0-4.

Preferred monomers of formula [2] are those wherein:

R$^2$, R$^3$ independently=H or CH$_3$;

W, W' independently=O(CH$_2$)$_d$, O(CH$_2$)$_d$C$_6$H$_4$, or nothing;

J=O(CH$_2$CH$_2$O)$_b$ or nothing, provided that if W and W'=nothing, then J≠nothing;

d=0-6; and b=1-10.

Preferred macromers of formula [3] are those wherein:

e=2-40;

X=—O— or —N(CH$_3$)—;

Y=(CH$_2$CH$_2$O)$_q$CH$_3$, —(CH$_2$CH$_2$O)$_q$H, or —(CH$_2$CH$_2$O)$_q$C$_6$H$_5$;

q=2-23;

T, T' independently=O(CH$_2$)$_{d'}$ or nothing;

K=O(CH$_2$CH$_2$O)$_{b'}$ or nothing, provided that if T and T'=nothing, then K≠nothing;

d'=0-6;

b'=1-10;

L=H, Cl, Br, —CH$_2$C(O)C$_6$H$_5$, —CH$_2$C(O)C$_6$H$_4$OH, —CH$_2$C(O)C$_6$H$_4$OCH$_3$, or —CH$_2$CH=CH$_2$;

R$^4$, R$^5$ independently=H, CH$_3$, or CH$_2$CH$_3$;

R$_6$=—CO$_2$CH$_3$, —CO$_2$CH$_2$CH$_3$, —CN, or —CONHCH$_2$CH$_2$CH$_2$CH$_3$;

R$^7$, R$^8$ independently=H or CH$_3$; and a''=2-12.

Most preferred macromers of formula [3] are those wherein:

e=5-30;

X=—O—;

Y=(CH$_2$CH$_2$O)$_q$CH$_3$;

q=4-15;

T, T' independently=O(CH$_2$)$_{d'}$, O(CH$_2$)$_d$C$_6$H$_4$, or nothing;

K=O(CH$_2$CH$_2$O)$_{b'}$ or nothing, provided that if T and T'=nothing, then K 0 nothing;

d'=0-6;

b'=1-10;

L=H, —CH$_2$C(O)C$_6$H$_5$, —CH$_2$C(O)C$_6$H$_4$OCH$_3$, or —CH$_2$CH=CH$_2$;

R$^4$, R$^5$ independently=H, CH$_3$, or CH$_2$CH$_3$;

R$_6$=—CO$_2$CH$_3$, —CO$_2$CH$_2$CH$_3$, —CN, or —CONHCH$_2$CH$_2$CH$_2$CH$_3$;

R$^7$, R$^8$ independently=H or CH$_3$; and a''=2-12.

Monomers of formula [1] are known and can be made by known methods. See, for example, U.S. Pat. Nos. 5,331,073 and 5,290,892. Many monomers of formula [1] are commercially available from a variety of sources. Preferred monomers of formula [1] include benzyl methacrylate; 2-phenylethyl methacrylate; 3-phenylpropyl methacrylate; 4-phenylbutyl methacrylate; 5-phenylpentyl methacrylate; 2-phenoxyethyl methacrylate; 2-(2-phenoxyethoxy)ethyl methacrylate; 2-benzyloxyethyl methacrylate; 2-(2-(benzyloxy)ethoxy)ethyl methacrylate; and 3-benzyloxypropyl methacrylate; and their corresponding acrylates.

Monomers of formula [2] are known and can be made by known methods. Many are commercially available. Preferred monomers of formula [2] include ethylene glycol dimethacrylate; diethylene glycol dimethacrylate; triethylene glycol dimethacrylate; 1,6-hexanediol dimethacrylate; 1,4-butanediol dimethacrylate; 1,4-benzenedimethanol dimethacrylate; and their corresponding acrylates. Most preferred is 1,4-butanediol diacrylate.

Macromers of formula [3] can be made by known methods. They are commercially available in some instances and can be made by known methods. Macromonomers of formula [3] can be made by covalently attaching a polymerizable group to a functional end group of a linear or branched acrylic or methacrylic polymer. For example, a hydroxyl terminated poly(alkyl methacrylate) may be synthesized by anionic polymerization using an initiator containing a protected hydroxyl group, that following deprotection, is reacted with, for example, methacryloyl chloride or methacrylic acid to produce macromer [3a]. The terminal hydroxyl group may also be reacted with other reagents, for example isocyanatoethyl methacrylate or vinyl benzyl chloride, to produce a terminal polymerizable group. See, generally, U.S. Pat. Nos. 6,221,991, 3,862,077 and 3,842,059, the entire contents of which are incorporated by reference. Alternatively, the polymerization may be terminated with an aldehyde and subsequently reacted with methacryloyl chloride to produce functional macromer [3b] (See for example, U.S. Pat. Nos. 6,221,991 and 5,391,628).

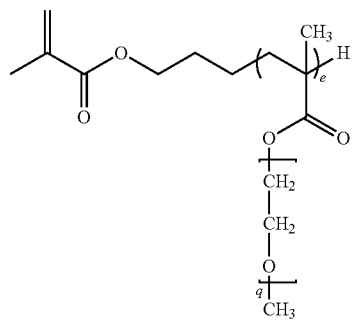

[3a]

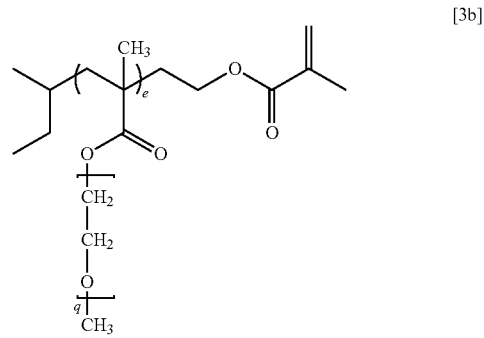

[3b]

Macromers of formula [3c] can also be prepared using atom transfer radical polymerization (ATRP) conditions. For example, a hydroxyl terminal initiator (hydroxyethyl bromoisobutyrate) can combined with copper(I) halide and a solubilizing amine ligand. This can be used to initiate the polymerization of an acrylate or methacrylate monomer. The resulting hydroxyl terminated poly(acrylate) or poly(methacrylate) can then be reacted with methacryloyl chloride or isocyanatoethyl methacrylate. See, generally, U.S. Pat. Nos. 5,852,129, 5,763,548, and 5,789,487, and Neugebauer, et al., "Densely-grafted and double-grafted PEO brushes via ATRP. A route to soft elastomers," Macromolecules 2003, 36, 6746-6755; Ishizu, et al., "Aggregation behaviors of AB-type brush-block-brush amphiphilic copolymers in aqueous media," Journal of Materials Science 2004, 39, 4295-4300; Kurjata, et al., "Synthesis of poly[dimethylsiloxane-block-oligo(ethylene glycol) methyl ether methacrylate]: an amphiphilic copolymer with a comb-like block," Polymer 2004, 45, 6111-6121; and Wang, et al., "Facile Atom Transfer Radical Polymerization of Methoxy-Capped Oligo(ethylene glycol) Methacrylate in Aqueous Media at Ambient Temperature," Macromolecules 2000, 33, 6640-6647. Alternatively, a catalytic chain transfer reagent may be used in conjunction with living polymerization techniques to produce methacrylic macromonomers of formula [3d]. See for example Norman, J. et al. *Macromolecules* 2002, 35, 8954-8961, or Bon, S. A. F. et al. *J. Polym. Sci., Polym. Chem.* 2000, 38, 2678. Macromers of formula [3e] may be produced, for example, by polymerization in the presence of a thiol functional chain transfer agent followed by reaction with methacryloyl chloride or isocyanatoethyl methacrylate. For example, see Chen, G.-F. et al. *Macromolecules* 1991, 24, 2151.

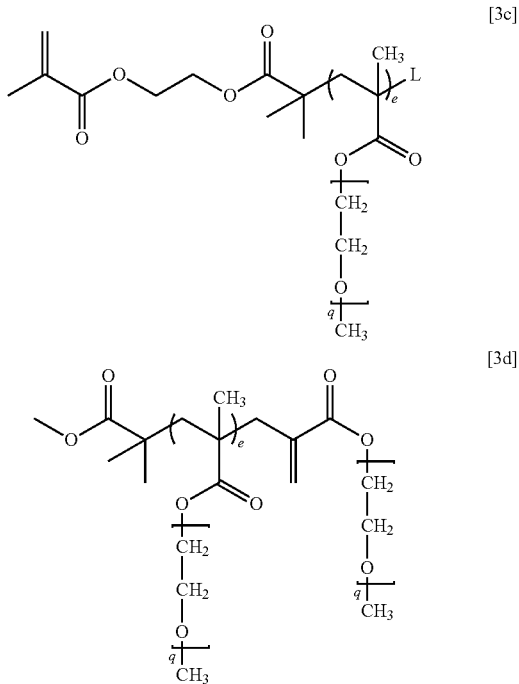

The copolymeric materials of the present invention contain a total amount of monomer [1] in an amount from 70 to 98%, preferably from 80 to 95%. The difunctional cross-linker [2] concentration can be on the order of 0.5 to 3% of the total concentration, and preferably from 1 to 2%.

The materials of the present invention have at least one macromer of [3]. The total amount of macromer [3] depends on the desired physical properties for the device materials. The copolymeric materials of the present invention contain a total of at least 0.5 wt % and can contain as much as 15% of macromer [3]. Preferably, the copolymeric device materials will contain 1-10 wt % of macromer [3]. More preferably, the device materials will contain 1-5 wt % of macromer [3]. Most preferably, the device materials will contain 2-4 wt % of macromer [3].

The copolymeric device materials of the present invention optionally contain one or more ingredients selected from the group consisting of polymerizable UV absorbers and polymerizable colorants. Preferably, the device material of the present invention contains no other ingredients besides the monomers of formulas [1] and [2], the macromer [3], and the optional polymerizable UV absorbers and polymerizable colorants.

Reactive UV absorbers are known. A suitable reactive UV absorber is 2-(2'-hydroxy-3'-methallyl-5'-methylphenyl)benzotriazole, commercially available as o-Methallyl Tinuvin P ("oMTP") from Polysciences, Inc., Warrington, Pa. UV absorbers are typically present in an amount from about 0.1-5%. Suitable reactive blue-light absorbing compounds include those described in U.S. Pat. No. 5,470,932. Blue-light absorbers are typically present in an amount from about 0.01-0.5%. When used to make IOLs, the device materials of the present invention preferably contain both a reactive UV absorber and a reactive colorant.

In order to form the device material of the present invention, the chosen ingredients [1], [2], and [3], along with any of the optional ingredients, are combined and polymerized using a radical initiator to initiate polymerization by the action of either heat or radiation. The device material is preferably polymerized in de-gassed polypropylene molds under nitrogen or in glass molds.

Suitable polymerization initiators include thermal initiators and photoinitiators. Preferred thermal initiators include peroxy free-radical initiators, such as t-butyl (peroxy-2-ethyl) hexanoate and di-(tert-butylcyclohexyl) peroxydicarbonate (commercially available as Perkadox® 16 from Akzo Chemicals Inc., Chicago, Ill.). Particularly in cases where the materials of the present invention do not contain a blue-light absorbing chromophore, preferred photoinitiators include benzoylphosphine oxide initiators, such as 2,4,6-trimethylbenzoyldiphenyl-phosphine oxide, commercially available as Lucirin® TPO from BASF Corporation (Charlotte, N.C.). Initiators are typically present in an amount equal to about 5% or less of the total formulation weight, and more preferably less than 2% of the total formulation. As is customary for purposes of calculating component amounts, the initiator weight is not included in the formulation weight % calculation.

The particular combination of the ingredients described above and the identity and amount of any additional components are determined by the desired properties of the finished device material. In a preferred embodiment, the device materials of the present invention are used to make IOLs having an optic diameter of 5.5 or 6 mm that are designed to be compressed or stretched and inserted through surgical incision sizes of 2 mm or less. For example, the macromonomer [3] is combined with a mono-functional acrylate or methacrylate monomer [1], a multifunctional acrylate or methacrylate cross-linker [2], a reactive UV absorber and a reactive colorant and copolymerized using a radical initiator in a suitable lens mold.

The device material preferably has a refractive index in the hydrated state of at least about 1.50, and more preferably at least about 1.53, as measured by an Abbe' refractometer at 589 nm (Na light source) and 25° C. Optics made from materials having a refractive index lower than 1.50 are necessarily thicker than optics of the same power which are made from materials having a higher refractive index. As such, IOL optics made from materials with comparable mechanical properties and a refractive index lower than about 1.50 generally require relatively larger incisions for IOL implantation.

The proportions of the monomers and macromer to be included in the copolymers of the present invention should be chosen so that the copolymer has a glass transition temperature ($T_g$) not greater than about 37° C., which is normal human body temperature. Copolymers having glass transition temperatures higher than 37° C. are not suitable for use in foldable IOLs; such lenses could only be rolled or folded at temperatures above 37° C. and would not unroll or unfold at normal body temperature. It is preferred to use copolymers having a glass transition temperature somewhat below normal body temperature and no greater than about normal room temperature, e.g., about 20-25° C., in order that IOLs made of such copolymers can be rolled or folded conveniently at room temperature. $T_g$ is measured by differential scanning calorimetry at 10° C./min., and is determined at the midpoint of the transition of the heat flux curve.

For IOLs and other applications, the materials of the present invention must exhibit sufficient strength to allow devices made of them to be folded or manipulated without fracturing. Thus the copolymers of the present invention will have an elongation of at least 80%, preferably at least 100%, and most preferably greater than 110%. This property indicates that lenses made of such materials generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions using an Instron Material Tester (Model No. 4442 or equivalent) with a 50 Newton load cell. The grip distance is set at 14 mm and a crosshead speed is set at 500 mm/minute and the sample is pulled until failure. The elongation (strain) is reported as a fraction of the displacement at failure to the original grip distance. Since the materials to be tested are essentially soft elastomers, loading them into the Instron machine tends to make them buckle. To remove the slack in the material sample a pre-load is placed upon the sample. This helps to reduce the slack and provide a more consistent reading. Once the sample is pre-loaded to a desired value (typically 0.03 to 0.05 N) the strain is set to zero and the test begun. The modulus is calculated as the instantaneous slope of the stress-strain curve at 0% strain ("Young's modulus"), 25% strain ("25% modulus") and 100% strain ("100% modulus).

IOLs made of the ophthalmic device materials of the present invention are more resistant to glistenings than other materials. Glistenings are measured according to the following test. The presence of glistenings is measured by placement of a lens or disk sample into a vial or sealed glass chamber and adding deionized water or a balanced salt solution. The vial or glass chamber is then placed into a water bath preheated to 45° C. Samples are to be maintained in the bath for a minimum of 16 hours and preferably 24±2 hours. The vial or glass chamber is then cooled to ambient temperature for a minimum of 60 minutes and preferably 90±30 minutes. The sample is inspected visually in various on angle or off angle lighting to evaluate clarity. Visualization of glistenings is carried out at ambient temperature with a light microscope using a magnification of 50 to 200×. A sample is judged to have many glistenings if, at 50-200× magnification, there are approximately 50 to 100% as many glistenings as observed in control samples based on 65 weight % 2-phenylethyl acrylate, 30 weight % 2-phenylethyl methacrylate, 3.2 weight % 1,4-butanediol diacrylate, and 1.8 weight % oMTP. Similarly, a sample is judged to have few glistenings if there are approximately 10% or more glistenings relative to the quantity observed in control samples. A sample is judged to have very few glistenings if there are approximately 1% or more glistenings relative to a control sample. A sample is judged to be free of glistenings if the number of glistenings detected in the eyepiece is zero. A sample is judged to be substantially free of glistenings if, at 50-200× magnification, the number of glistenings detected in the eyepiece is less than about 2/mm$^3$. It is often very difficult to detect glistenings, especially at surfaces and edges where more defects and debris have formed, so the sample is rastered throughout the entire volume of the lens, varying the magnification levels (50-200×), the aperture iris diaphragm, and the field conditions (using both bright field and dark field conditions) in an attempt to detect the presence of glistenings.

The copolymers of the present invention most preferably have an equilibrium water content (EWC) of 0.5-3.0%. EWC may be gravimetrically determined by comparison of dry and hydrated sample weight. First, the dry sample weight is obtained, then the sample is placed in a suitable container and equilibrated in de-ionized H$_2$O at a prescribed temperature for at least 24 h. The sample is then removed from the de-ionized H$_2$O, excess surface water is removed and the sample is weighed. EWC is determined by the following formula: % EWC=[(wt$_{hyd}$−wt$_{dry}$)/wt$_{hyd}$]×100

IOLs constructed of the device materials of the present invention can be of any design capable of being stretched or compressed into a small cross section that can fit through a 2-mm incision. For example, the IOLs can be of what is known as a one-piece or multi-piece design, and comprise optic and haptic components. The optic is that portion which serves as the lens and the haptics are attached to the optic and are like arms that hold the optic in its proper place in the eye. The optic and haptic(s) can be of the same or different material. A multi-piece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use as other ophthalmic or otorhinolaryngological devices such as contact lenses, keratoprostheses, corneal inlays or rings, otological ventilation tubes and nasal implants.

The invention will be further illustrated by the following examples, which are intended to be illustrative, but not limiting.

EXAMPLE 1

All monomers, cross-linkers and initiators were purchased from commercial sources. Macromer [3] ("polyPEG-MA") was synthesized from poly(ethylene glycol) 550 monomethyl ether monomethacrylate ("PEG-MA 550"). Two macromer [3] molecular weights were used: "polyPEG-MA 4.1 k"

(GPC $M_n$ 4,112; $M_w/M_n$ of 1.80; e=7 (calculated as 4112/550)) and "polyPEG-MA 10.3 k" (GPC $M_n$ 10,300; $M_w/M_n$ of 1.44; e=19). 2-phenylethyl methacrylate (PEMA) and benzyl methacrylate (BzMA) were each passed through basic alumina and degassed with $N_2$ prior to use. 2-Phenylethyl acrylate ("PEA"), benzyl acrylate ("BzA"), and 1,4-butanediol diacrylate ("BDDA") were purified by column chromatography prior to use. 2,2-Azobisisobutyronitrile ("AIBN") was recrystallized from methanol prior to use. Di-(4-t-butyl-cyclohexyl)peroxydicarbonate ("Perkadox® 16S"), 2-(2'-Hydroxy-3'-t-butyl-5'-(3''-(2'''-hydroxy-3'''methacryloyloxypropoxy)propoxy)phenyl)-5-methoxy-2H-benzotriazole ("UV13"), and ortho-methallyl Tinuvin®P ("oMTP") were used as received.

Polypropylene molds were vacuum de-gassed at 90° C. prior to use. The molds were placed in a nitrogen atmosphere glove box immediately after degassing. The monomer(s), macromer, and cross-linker were combined as indicated in Table 1. AIBN or Perkadox® 16S initiator was added (0.5-2.0 wt. %), the solution was mixed thoroughly then placed under low vacuum to remove any trapped air bubbles, back-flushed with nitrogen, and immediately placed in the glove box. The monomer formulation was dispensed into vacuum de-gassed polypropylene molds using a syringe equipped with a 0,2-μm PTFE filter. The filled molds were placed in a convection oven for 1 hr at 70° C., then 2 hrs at 110° C. The resulting polymer samples were removed from the molds and extracted in refluxing acetone for 6 hours, rinsed and air dried, then placed under vacuum at 70° C. for at least 15 hrs. Tensile properties, $T_g$, EWC, glistening resistance, and refractive index were determined according to the methods described above. The results are listed in Table 2.

TABLE 1

Formulation Component Detail

| ID | PEA (wt %) | BzA (wt %) | PEMA (wt %) | BzMA (wt %) | BDDA (wt %) | UV13 (wt %) | oMTP (wt %) | PolyPEG-MA 4.1k (wt %) | PolyPEG-MA 10.3k (wt %) |
|---|---|---|---|---|---|---|---|---|---|
| 0 | 65.0 | — | 30.0 | — | 3.2 | — | 1.8 | 0.0 | — |
| 1 | 63.1 | — | 29.1 | — | 3.1 | — | 1.7 | 3.0 | — |
| 2 | 61.1 | — | 28.2 | — | 3.0 | — | 1.7 | 6.0 | — |
| 3 | 59.2 | — | 27.3 | — | 2.9 | — | 1.6 | 9.0 | — |
| 4 | 89.00 | — | — | — | 1.00 | — | — | 10.00 | — |
| 5 | 78.99 | — | — | — | 1.00 | — | — | 20.00 | — |
| 6 | 67.48 | — | 20.00 | 10.00 | 1.52 | — | — | 1.01 | — |
| 7 | 66.47 | — | 19.99 | 10.00 | 1.52 | — | — | 2.02 | — |
| 8 | 65.48 | — | 19.99 | 9.99 | 1.52 | — | — | 3.01 | — |
| 9 | 64.47 | — | 20.02 | 9.99 | 1.51 | — | — | 4.00 | — |
| 10 | 63.50 | — | 19.99 | 10.00 | 1.50 | — | — | 5.01 | — |
| 11 | — | 97.99 | — | — | 1.01 | — | — | 1.00 | — |
| 12 | 10.00 | 88.01 | — | — | 1.00 | — | — | 1.00 | — |
| 13 | — | 96.50 | — | — | 1.50 | — | — | 2.00 | — |
| 14 | — | 95.49 | — | — | 1.50 | — | — | 3.02 | — |
| 15 | — | 95.98 | — | — | 2.00 | — | — | 2.02 | — |
| 16 | — | 94.96 | — | — | 2.03 | — | — | 3.01 | — |
| 17 | — | 90.48 | — | 5.00 | 1.50 | — | — | 3.02 | — |
| 18 | — | 95.47 | — | — | 1.51 | — | — | — | 3.02 |
| 19 | — | 93.46 | — | 2.01 | 1.51 | — | — | 3.03 | — |
| 20 | — | 93.24 | — | 2.25 | 1.51 | — | — | 3.00 | — |
| 21 | — | 92.49 | — | 3.01 | 1.51 | — | — | 3.00 | — |
| 22 | — | 91.47 | — | 4.00 | 1.51 | — | — | 3.01 | — |
| 23 | — | 87.99 | — | 7.50 | 1.51 | — | — | 3.00 | — |
| 24 | — | 85.49 | — | 10.01 | 1.50 | — | — | 3.00 | — |
| 25 | — | 83.68 | — | 10.01 | 1.50 | 1.80 | — | 3.00 | — |

TABLE 2

Tensile and Thermal Properties, % EWC and Glistening Test Results

| ID | Tensile Strength (MPa) | Strain at Break (MPa) | Young's Modulus (MPa) | 100% Secant Modulus (MPa) | EWC (%) | Glistenings | $T_g$ (° C.) | RI (22° C., dry) |
|---|---|---|---|---|---|---|---|---|
| 0 | 8.12 | 104 | 57.30 | 7.51 | 0.30 | Many | 9.5 | — |
| 1 | 8.34 | 114 | 40.87 | 6.39 | 0.66 | None | 6.6 | 1.5537 |
| 2 | 6.23 | 110 | 19.89 | 4.94 | 1.68 | None | 2.4 | 1.5513 |
| 3 | — | — | — | — | 2.69 | None | −0.9 | 1.5480 |
| 4 | 1.56 | 163 | 1.56 | 0.65 | 3.92 | None | — | 1.5457 |
| 5 | 0.92 | 132 | 1.02 | 0.63 | 9.78 | None | — | 1.5375 |
| 6 | 8.53 | 174 | 48.07 | 3.63 | 0.50 | Few | — | 1.5562 |
| 7 | 8.57 | 177 | 37.57 | 3.22 | 0.75 | None | 7.5 | 1.5553 |
| 8 | 7.65 | 173 | 28.43 | 2.78 | 1.00 | None | — | 1.5545 |
| 9 | 7.39 | 174 | 23.99 | 2.52 | 1.32 | None | — | 1.5536 |
| 10 | 6.42 | 167 | 18.53 | 2.27 | 1.61 | None | — | 1.5528 |
| 11 | 9.77 | 252 | 39.94 | 2.20 | 0.46 | Few | — | 1.5644 |
| 12 | 8.53 | 246 | 25.62 | 1.73 | 0.48 | Few | — | 1.5633 |

TABLE 2-continued

Tensile and Thermal Properties, % EWC and Glistening Test Results

| ID | Tensile Strength (MPa) | Strain at Break (MPa) | Young's Modulus (MPa) | 100% Secant Modulus (MPa) | EWC (%) | Glistenings | $T_g$ (°C.) | RI (22° C., dry) |
|----|----|----|----|----|----|----|----|----|
| 13 | 6.20 | 183 | 12.90 | 1.62 | 0.85 | Very Few | — | 1.5633 |
| 14 | 6.24 | 183 | 10.25 | 1.51 | 1.10 | None | — | 1.5621 |
| 15 | 6.91 | 160 | 12.39 | 2.11 | 0.81 | Very Few | — | 1.5630 |
| 16 | 6.69 | 158 | 11.64 | 2.10 | 1.06 | None | — | 1.5615 |
| 17 | 10.73 | 201 | 56.72 | 3.40 | 0.89 | None | — | 1.5620 |
| 18 | 9.41 | 197 | 38.55 | 2.72 | 1.37 | Very Few | — | 1.5610 |
| 19 | 8.91 | 190 | 38.54 | 2.75 | 1.08 | None | — | 1.5620 |
| 20 | 8.91 | 190 | 30.52 | 2.39 | 0.91 | None | — | — |
| 21 | 9.60 | 192 | 45.32 | 2.95 | 1.02 | None | — | 1.5622 |
| 22 | 9.86 | 191 | 50.74 | 3.19 | 1.00 | None | — | 1.5622 |
| 23 | 9.70 | 184 | 56.25 | 3.56 | 1.25 | None | — | — |
| 24 | 10.29 | 184 | 62.28 | 4.03 | 1.06 | None | 13.347 | — |
| 25 | — | — | — | — | 0.93 | None | — | 1.5636 |

EXAMPLE 2

The copolymers shown in Table 3, which contained varying sizes of PEG-containing additive (PEG-MA 550, PolyPEG-MA 4.1 k, and PolyPEG-MA 10.3 k), were prepared in the manner described in Example 1. Tensile properties, EWC, glistening resistance, and refractive index were determined according to the methods described above. The results are listed in Table 4.

TABLE 3

Comparative Examples Formulation Component Detail

| ID | BzA (wt %) | BDDA (wt %) | PEG-MA 550 (wt %) | PolyPEG-MA 4.1k (wt %) | PolyPEG-MA 10.3k (wt %) |
|----|----|----|----|----|----|
| 26 | 93.47 | 1.51 | 5.02 | — | — |
| 27 | 93.47 | 1.51 | — | 5.02 | — |
| 28 | 93.49 | 1.51 | — | — | 5.00 |

TABLE 4

Comparative Formulation Tensile and Thermal Properties, % EWC and Glistening Test Results

| ID | Tensile Strength (MPa) | Strain at Break (MPa) | Young's Modulus (MPa) | 100% Secant Modulus (MPa) | EWC (%) | Glistenings | RI (22° C., dry) |
|----|----|----|----|----|----|----|----|
| 26 | 6.87 | 191 | 12.79 | 1.64 | 0.59 | Many | 1.5598 |
| 27 | 7.49 | 189 | 16.25 | 1.85 | 1.50 | None | 1.5604 |
| 28 | 8.92 | 199 | 25.32 | 2.22 | 2.35 | None | 1.5595 |

EXAMPLE 3

The copolymers shown in Table 5, which contained varying molecular weights of the polyPEG-MA additive: "polyPEG-MA 3570" (GPC $M_n$ 3570; $M_w/M_n$ of 1.42; e=6), "polyPEG-MA 4012" (GPC $M_n$ 4012; $M_w/M_n$ 1.54; e=7), "polyPEG-MA 4141" (GPC $M_n$ 4141; $M_w/M_n$ 1.50; e=8), and polyPEG-MA 3708 (GPC $M_n$ 3708; $M_w/M_n$ 1.49; e=7) were prepared in the manner described in Example 1. Tensile properties, EWC, glistening resistance, and refractive index were determined according to the methods described above. The results are listed in Table 6.

TABLE 5

Formulation Component Detail

| ID | BzA (wt %) | BzMA (wt %) | BDDA (wt %) | PEG-MA 550 (wt %) | PolyPEG-MA 3570 (wt %) | PolyPEG-MA 4012 (wt %) | PolyPEG-MA 4141 (wt %) | PolyPEG-MA 3708 (wt %) |
|----|----|----|----|----|----|----|----|----|
| 29 | 85.47 | 9.99 | 1.52 | 3.02 | — | — | — | — |
| 30 | 83.46 | 9.99 | 1.51 | 5.03 | — | — | — | — |
| 31 | 78.49 | 10.01 | 1.50 | 10.00 | — | — | — | — |
| 32 | 73.50 | 10.00 | 1.51 | 15.00 | — | — | — | — |
| 33 | 68.50 | 10.00 | 1.50 | 20.00 | — | — | — | — |
| 34 | 85.46 | 10.00 | 1.53 | — | 3.00 | — | — | — |
| 35 | 83.47 | 10.02 | 1.50 | — | 5.01 | — | — | — |
| 36 | 85.38 | 9.99 | 1.61 | — | — | 3.02 | — | — |
| 37 | 85.47 | 10.00 | 1.50 | — | — | — | 3.03 | — |
| 38 | 85.40 | 10.01 | 1.52 | — | — | — | — | 3.07 |

TABLE 6

Tensile and Thermal Properties, % EWC and Glistening Test Results

| ID | Tensile Strength (MPa) | Strain at Break (MPa) | Young's Modulus (MPa) | 100% Secant Modulus (MPa) | EWC (%) | Glistenings | RI (22° C., dry) |
|---|---|---|---|---|---|---|---|
| 29 | 8.26 | 175 | 38.99 | 3.42 | 0.46 | Many | 1.5631 |
| 30 | 6.67 | 170 | 18.07 | 2.33 | 0.55 | Many | 1.5611 |
| 31 | 3.94 | 151 | 9.25 | 1.51 | 0.79 | Few | 1.5566 |
| 32 | 2.79 | 134 | 8.44 | 1.42 | 1.19 | Very Few | 1.5518 |
| 33 | 2.41 | 126 | 2.59 | 1.47 | 3.38 | None | 1.5493 |
| 34 | 8.23 | 167 | 46.35 | 3.94 | 0.74 | None | 1.5630 |
| 35 | 7.47 | 169 | 26.69 | 3.04 | 1.21 | None | 1.5608 |
| 36 | 8.60 | 163 | 45.02 | 4.29 | 0.88 | None | 1.5626 |
| 37 | 8.19 | 167 | 45.24 | 4.04 | 0.90 | None | 1.5627 |
| 38 | 8.94 | 173 | 44.30 | 4.07 | 0.79 | None | 1.5626 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A polymeric ophthalmic or otorhinolaryngological device material formed by polymerizing a composition comprising a) 70 to 98% (w/w) of a monofunctional acrylate or methacrylate monomer of formula [1]:

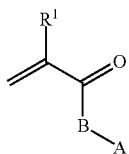

[1]

wherein
B=—O(CH$_2$)$_n$—, —(OCH$_2$CH$_2$)$_n$—, —NH(CH$_2$)$_n$—, or —NCH$_3$(CH$_2$)$_n$—;
R$^1$=H, CH$_3$, CH$_2$CH$_3$, or CH$_2$OH;
n=0-12;
A=C$_6$H$_5$ or O(CH$_2$)$_m$C$_6$H$_5$, where the C$_6$H$_5$ group is optionally substituted with —(CH$_2$)$_n$H, —O(CH$_2$)$_n$H, —CH(CH$_3$)$_2$, —C$_6$H$_5$, —OC$_6$H$_5$, —CH$_2$C$_6$H$_5$, F, Cl, Br, or I; and
m=0-18;

b) a difunctional acrylate or methacrylate cross-linking monomer of formula [2]:

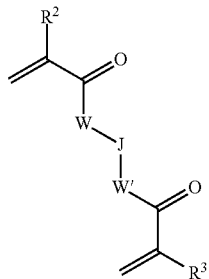

[2]

wherein
R$^2$, R$^3$ independently=H, CH$_3$, CH$_2$CH$_3$, or CH$_2$OH;
W, W' independently=O(CH$_2$)$_d$, NH(CH$_2$)$_d$, NCH$_3$(CH$_2$)$_d$, O(CH$_2$)$_d$C$_6$H$_4$, O(CH$_2$CH$_2$O)$_d$CH$_2$, O(CH$_2$CH$_2$CH$_2$O)$_d$CH$_2$, O(CH$_2$CH$_2$CH$_2$CH$_2$O)$_d$CH$_2$, or nothing;
J=(CH$_2$)$_a$, O(CH$_2$CH$_2$O)$_b$, O, or nothing, provided that if W and W'=nothing, then J≠nothing;
d=0-12;
a=1-12; and
b=1-24;
and c) 2 to 4% (w/w) of a hydrophilic side-chain macromer of formula [3c]:

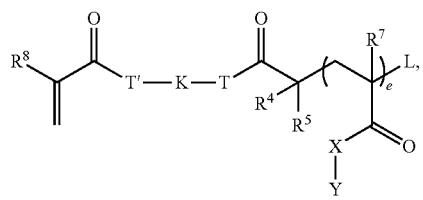

[3c]

wherein for formula [3c]:
e=1-50;
X=—O—, NH—, —N(CH$_3$)—, —N(CH$_2$CH$_3$)—, or —N(C$_6$H$_5$)—;
Y=—H, —(CH$_2$)$_p$OH, —CH$_2$CH$_2$N(CH$_3$)$_2$, —CH$_2$CH$_2$N(CH$_2$CH$_3$)$_2$, —CH$_2$CH(OH)CH$_2$OH, —(CH$_2$CH$_2$O)$_p$CH$_3$, —(CH$_2$CH$_2$O)$_p$H, —(CH$_2$CH$_2$O)$_p$C$_6$H$_5$, or

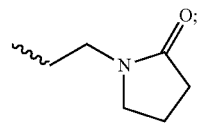

p=1-12;
q=1-230;
T, T' independently=O(CH$_2$)$_d$, NH(CH$_2$)$_d$, NCH$_3$(CH$_2$)$_d$, O(CH$_2$)$_d$C$_6$H$_4$, O(CH$_2$CH$_2$O)$_d$CH$_2$, O(CH$_2$CH$_2$CH$_2$O)$_d$CH$_2$, O(CH$_2$CH$_2$CH$_2$CH$_2$O)$_d$CH$_2$, or nothing;
K=(CH$_2$)$_{a'}$, O(CH$_2$CH$_2$O)$_{b'}$, O, or nothing, provided that if T and T'=nothing, then K≠nothing;
d'=0-12;
a'=1-12;
b'=1-24;
L=H, Cl, Br, —CH$_2$C(O)CH$_3$, CH$_2$C(O)C(CH$_3$)$_3$, —CH$_2$C(O)C$_6$H$_5$, —CH$_2$C(O)C$_6$H$_4$OH, —CH$_2$C(O)C$_6$H$_4$OCH$_3$,

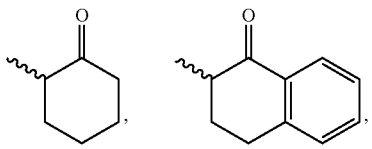

or —CH$_2$CH=CH$_2$;
R$^4$, R$^5$ independently=H, CH$_3$, CH$_2$CH$_3$, CH$_2$CH$_2$CH$_3$, CH(CH$_3$)$_2$, CH$_2$CH$_2$CH$_2$CH$_3$, or CH$_2$CH(CH$_3$)$_2$; and
R$^7$=H, CH$_3$, CH$_2$CH$_3$, or CH$_2$OH.

2. The polymeric device material of claim 1 wherein for the monomer of formula [1]:
B=—O(CH$_2$)$_n$— or —(OCH$_2$CH$_2$)$_n$—;
R$^1$=—H or —CH$_3$;
n=1-5;
A=—C$_6$H$_5$, O(CH$_2$)$_m$C$_6$H$_5$; and
m=0-4.

3. The polymeric device material of claim 1 wherein for the monomer of formula [2]:
R$^2$, R$^3$ independently=H or CH$_3$;
W, W' independently=O(CH$_2$)$_d$, O(CH$_2$)$_d$C$_6$H$_4$, or nothing;
J=O(CH$_2$CH$_2$O)$_b$ or nothing, provided that if W and W'=nothing, then J≠nothing;
d=0-6; and
b=1-10.

4. The polymeric device material of claim 1 wherein for the macromer of formula [3]:
e=2-40;
X=—O— or —N(CH$_3$)—;
Y=(CH$_2$CH$_2$O)$_q$CH$_3$, —(CH$_2$CH$_2$O)$_q$H, or —(CH$_2$CH$_2$O)$_q$C$_6$H$_5$;
q=2-23;
T, T' independently=O(CH$_2$)$_{d'}$ or nothing;
K=O(CH$_2$CH$_2$O)$_{b'}$ or nothing, provided that if T and T'=nothing, then K≠nothing;
d'=0-6;
b'=1-10;
L=H, Cl, Br, —CH$_2$C(O)C$_6$H$_5$, —CH$_2$C(O)C$_6$H$_4$OH, —CH$_2$C(O)C$_6$H$_4$OCH$_3$, or —CH$_2$CH=CH$_2$;
R$^4$, R$^5$ independently=H, CH$_3$, or CH$_2$CH$_3$; and
R$^7$=H or CH$_3$.

5. The polymeric device material of claim 4 wherein for the macromer of formula [3]:
e=5-30;
X=—O—;
Y=(CH$_2$CH$_2$O)$_q$CH$_3$;
q=4-15;
T, T' independently=O(CH$_2$)$_{d'}$ or nothing;
K=O(CH$_2$CH$_2$O)$_{b'}$ or nothing, provided that if T and T'=nothing, then K≠nothing;
d'=0-6;
b'=1-10;
L=H, —CH$_2$C(O)C$_6$H$_5$, —CH$_2$C(O)C$_6$H$_4$OCH$_3$, or —CH$_2$CH=CH$_2$;
R$^4$, R$^5$ independently=H, CH$_3$, or CH$_2$CH$_3$; and
R$^7$=H or CH$_3$.

6. The polymeric device material of claim 1 wherein the monomer of formula [1] is selected from the group consisting of benzyl methacrylate; 2-phenylethyl methacrylate; 3-phenylpropyl methacrylate; 4-phenylbutyl methacrylate; 5-phenylpentyl methacrylate; 2-phenoxyethyl methacrylate; 2-(2-phenoxyethoxy)ethyl methacrylate; 2-benzyloxyethyl methacrylate; 2-(2-(benzyloxy)ethoxy)ethyl methacrylate; 3-benzyloxypropyl methacrylate; benzyl acrylate; 2-phenylethyl acrylate; 3-phenylpropyl acrylate; 4-phenylbutyl acrylate; 5-phenylpentyl acrylate; 2-phenoxyethyl acrylate; 2-(2-phenoxyethoxy)ethyl acrylate; 2-benzyloxyethyl acrylate; 2-(2-(benzyloxy)ethoxy)ethyl acrylate; and 3-benzyloxypropyl acrylate.

7. The polymeric device material of claim 1 wherein the monomer of formula [2] is selected from the group consisting of ethylene glycol dimethacrylate; diethylene glycol dimethacrylate; triethylene glycol dimethacrylate; 1,6-hexanediol dimethacrylate; 1,4-butanediol dimethacrylate; 1,4-benzenedimethanol dimethacrylate; ethylene glycol diacrylate; diethylene glycol diacrylate; triethylene glycol diacrylate; 1,6-hexanediol diacrylate; 1,4-butanediol diacrylate; and 1,4-benzenedimethanol diacrylate.

8. The polymeric device material of claim 1 wherein the amount of monomer [1] is 80 to 95% (w/w).

9. The polymeric device material of claim 1 wherein the amount of monomer [2] is 0.5 to 3% (w/w).

10. The polymeric device material of claim 1 further comprising an ingredient selected from the group consisting of a polymerizable UV absorbers and a polymerizable colorants.

11. The polymeric device material of claim 10 comprising 0.1-5% (w/w) of a polymerizable UV absorber and 0.01-0.5% (w/w) of a polymerizable colorant.

12. An ophthalmic or otorhinolaryngological device comprising the polymeric device material of claim 1 wherein the ophthalmic or otorhinolaryngological device is selected from the group consisting of intraocular lenses; contact lenses; keratoprostheses; corneal inlays or rings; otological ventilation tubes; and nasal implants.

13. The ophthalmic or otorhinolaryngological device of claim 12 wherein the ophthalmic or otorhinolaryngological device is an intraocular lens.

* * * * *